United States Patent
Du et al.

(10) Patent No.: US 10,190,961 B2
(45) Date of Patent: Jan. 29, 2019

(54) SAMPLE ANALYZER AND SAMPLE ANALYZING METHOD THEREOF

(71) Applicant: SHENZHEN MINDRAY BIO-MEDICAL ELECTRONICS CO., LTD., Shenzhen (CN)

(72) Inventors: Xiansuan Du, Shenzhen (CN); Yong Dai, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 23 days.

(21) Appl. No.: 15/163,541

(22) Filed: May 24, 2016

(65) Prior Publication Data

US 2017/0315046 A1 Nov. 2, 2017

(30) Foreign Application Priority Data

Mar. 18, 2016 (CN) .......................... 2016 1 0156013

(51) Int. Cl.
| | |
|---|---|
| *G01N 15/14* | (2006.01) |
| *G01N 21/47* | (2006.01) |
| *G01N 21/64* | (2006.01) |
| *G01N 15/00* | (2006.01) |
| *G01N 15/10* | (2006.01) |

(52) U.S. Cl.
CPC ..... *G01N 15/1434* (2013.01); *G01N 15/1459* (2013.01); *G01N 21/4738* (2013.01); *G01N 21/6428* (2013.01); *G01N 2015/0076* (2013.01); *G01N 2015/0084* (2013.01); *G01N 2015/1006* (2013.01); *G01N 2015/1402* (2013.01); *G01N 2201/06113* (2013.01); *G01N 2201/124* (2013.01)

(58) Field of Classification Search
CPC ......... G01N 33/54366; G01N 2800/52; G01N 33/558; G01N 33/582; G01N 33/6893; G01N 35/00732; G01N 2035/00851; G01N 21/6486; G01N 27/3274; G01N 33/48721; G01N 33/5302; G01N 33/54373; G01N 33/56911
See application file for complete search history.

(56) References Cited

U.S. PATENT DOCUMENTS

| | | | | |
|---|---|---|---|---|
| 6,630,989 B1 * | 10/2003 | Caputo | ............. | G01N 33/5308 356/39 |
| 2003/0127333 A1 * | 7/2003 | Lauks | .................. | B01L 3/5023 204/600 |
| 2005/0123445 A1 * | 6/2005 | Blecka | ............... | G01N 35/0099 422/64 |

(Continued)

*Primary Examiner* — Michael P Stafira
(74) *Attorney, Agent, or Firm* — Polsinelli LLP; Kory D. Christensen

(57) ABSTRACT

A sample analyzer with an optical detection device and a sample analysis method of the sample analyzer are disclosed. The optical detection device includes a fluid chamber, a light source and a light detector. The fluid chamber includes an illumination zone. An analyte flows through the illumination zone so as to form a sample stream. The light source illuminates the illumination zone to excite cell articles, reacted with a reagent, of the sample stream to emit a light signal. The light detector detects the fluorescent lights and transforms it into an electric signal. The light detector can include a silicon photomultiplier.

16 Claims, 9 Drawing Sheets

(56) References Cited

U.S. PATENT DOCUMENTS

| | | | | |
|---|---|---|---|---|
| 2006/0073585 A1* | 4/2006 | McDevitt | ............... | C12Q 1/04 |
| | | | | 435/288.7 |
| 2006/0078998 A1* | 4/2006 | Puskas | ............... | G01N 21/6428 |
| | | | | 436/64 |
| 2008/0003685 A1* | 1/2008 | Goix | ............... | G01N 33/582 |
| | | | | 436/86 |
| 2008/0261242 A1* | 10/2008 | Goix | ............... | G01N 21/6428 |
| | | | | 435/7.21 |
| 2010/0173394 A1* | 7/2010 | Colston, Jr. | ............... | B01F 3/0807 |
| | | | | 435/287.2 |
| 2012/0122084 A1* | 5/2012 | Wagner | ............... | C12N 5/0612 |
| | | | | 435/6.1 |
| 2015/0268244 A1* | 9/2015 | Cho | ............... | G01N 15/1429 |
| | | | | 435/7.23 |

* cited by examiner

SAMPLE ANALYZER AND SAMPLE ANALYZING METHOD THEREOF

TECHNICAL FIELD

The present disclosure relates to a sample analysis technology, especially relating to a sample analyzer and a sample analysis method thereof.

BACKGROUND

A sample analyzer is used for analyzing cell articles of a biological analyte, such as classification and amount count for cell articles. The sample analyzer could be a blood analyzer or a flow cytometry.

The sample analyzer usually contains a sample collection device, a reagent supplement device, a sample reaction device, an optical measurement device and an analyte delivering device. The sample collection device collects the sample from outside of the sample analyzer and delivers the sample into the sample analyzer. The reagent supplement device draws reagents from outside of the sample analyzer and provides reagents to the sample reaction device. The sample and reagents are mixed and incubated in the sample reaction device to generate an analyte. The analyte is delivered to the optical measurement device by the analyte delivering device. The optical measurement device collects diffusion lights or fluorescent lights emitted from cell articles of the analyte illuminated by a light source, transforms the diffusion lights or fluorescent lights into electrical signals and implements classification and amount count for cell articles by analyzing the electrical signals.

Please refers to FIG. 1, by detecting side diffusion lights and fluorescent lights at the same time, the sample analyzer could be implemented for classification of white blood cells, such as 5 class classifications of white blood cells, which classifies white blood cells as lymphocytes, monocytes, neutrophils, eosinophils, and eosinophils.

The 5 class classifications of white blood cells could be conducted in one reaction test or in two reaction tests alternatively. For the classifications with two reaction tests, white blood cells are classified as 4 classes, which are lymphocytes, monocytes, eosinophils, and a cluster of neutrophils and eosinophils respectively in the first reaction test. Neutrophils and eosinophils are classified and counted in the second reaction test. The results from the first reaction test and the second reaction test then be combined to achieve 5 class classifications of white blood cells.

Immature granulocytes and reticulocytes of the analyte need to be detected in clinical trials. Please refers to FIG. 1, immature granulocytes are granulocytes still developing, granulocytes in early development stage contains more nuclein materials inside than mature one. With more nuclein materials, combination strength between a fluorescent dye and nuclein materials would be more solid so that strength of fluorescent lights emits under laser induction would be raised accordingly. Therefore, by identifying the specificity of fluorescent signals, the sample analyzer is able to detect immature granulocytes.

Please refers to FIG. 2, reticulocytes are red blood cells under immature stage. Reticulocytes contains a small amount of RNA, and the strength of fluorescent lights excited by a laser beam after reticulocytes are dyed by a fluorescent dye are stronger than fluorescent lights emitting from mature red blood cells. Therefore, by identifying the specificity of fluorescent signals, the sample analyzer is able to detect reticulocytes. Under above, detection of fluorescent light is very important for cells classification and amount count.

However, the excited fluorescent lights in the sample analyzer are quiet weak. For example, the strength of the fluorescent lights usually stays at pW or nW orders of magnitude. Therefore, sensitivity of the optical measurement device is demanded to satisfy very high standard to guarantee accuracy of fluorescent signals.

At present, a fluorescent light detector is usually implemented from vacuum photomultiplier or avalanche photodiode in common. Generally, fluorescent lights detector is operated through cooperating with a detection circuit. A specific structure of the fluorescent light detector is shown in FIG. 3, the fluorescent light detector includes a light detector, a gain circuit module, a signal adjustment module and an analog-digital (A/D) converter. The light detector includes a photoelectric transducer and a current gain portion. The gain circuit module includes a current-voltage transferring and amplifying circuit and a voltage amplifier.

Vacuum photomultiplier is with advantages of high sensitivity, high linear characteristic, high dynamic range and high signal/noise rate, and is able to detect fluorescent lights. However, vacuum photomultiplier has large size and is very expensive, which are disadvantages for system miniaturization and cost down of the sample analyzer.

Comparing with vacuum photomultiplier, avalanche photodiode is with advantages of small size and low cost. On the other hand, current gain of an avalanche photodiode relative to vacuum photomultiplier is too small so as to cause the sensitivity of avalanche photodiode becomes low correspondingly. For example, current gain of the vacuum photomultiplier generally reaches $10^5$-$10^6$, but current gain of avalanche photodiode is only 10-$10^2$ on the other hand. Therefore, sensitivity of the avalanche photodiode is hard to satisfy the requirements of fluorescent light detection. Therefore, an optical measurement device of a new sample analyzer with better performance/cost rate is demanded to satisfy clinical trials and solve above disadvantages.

SUMMARY

The application is for resolving at least one technical issues of the present technology. Therefore, a sample analyzer and a sample analysis method is provided at the present application.

A sample analyzer in the embodiments of this application includes:
a sample collection device collecting a sample quantitatively, wherein the sample comprises cell particles;
a reagent supplement device providing a reagent, wherein the reagent is able to react with the cell particles;
a sample reaction device receiving the sample from the sample collection device and the reagent from the reagent supplement device, wherein the reagent reacts with the cell particles to generate an analyte;
an analyte delivery device delivering the analyte for optical measurement;
an optical measurement device measuring a light signal generated from the analyte to generate a light signal information, wherein the optical measurement device comprises:
a fluid chamber comprising an illumination zone, wherein the analyte from the analyte delivery device flows through the illumination zone to form a sample stream;
a light source illuminating the illumination zone to make the light signal to be generated from the sample stream; and a light detector for detecting the light signal and transforming the light signal into the light signal information, wherein the light detector comprises at least one silicon photomultiplier.

In some embodiments, the sample analyzer includes a laser generator, the output power of the laser generator is between 1 to 20 mW. Preferably, the output power of the light source is selected from 5 to 15 mW.

In some embodiments, the sample analyzer includes a plurality of light sensing units arranged in an array configuration, the number of the light sensing units is larger or equal to 500 units. Preferably, the number of the light sensing units is larger or equal to 1000 units. Preferably, the number of the light sensing units is larger or equal to 1280 units.

In some embodiments, a light sensing area of the silicon photomultiplier is smaller than a threshold value, a distortion of a pulse amplitude of an electrical signal is triggered when the light sensing area of the silicon photomultiplier exceeds the threshold value, the electrical signal is generated according to an amount of dark pulse count overlapping on single one of the cell particles.

In some embodiments, a light sensing area of the silicon photomultiplier is between 1-36 mm$^2$. Preferably, the light sensing area is a circle with a diameter between 1.1 mm to 6.8 mm. Preferably, the light sensing area is a circle with a diameter between 2 mm to 6 mm. Preferably, the light sensing area is a square with a length between 1 mm to 6 mm. Preferably, the light sensing area is a square with a length of 3 mm.

In some embodiments, the optical measurement device includes an optical path, configured between the fluid chamber and the light detector, for converging the light signal to form a facula on a light sensing area of the silicon photomultiplier, the facula is between 50% to 78% of the light sensing area.

In some embodiments, the sample analyzer includes a controller for controlling a reverse bias voltage applied on the silicon photomultiplier to keep an overvoltage between 0 to 5 volt, the overvoltage is a difference between the reverse bias voltage and a breakdown voltage of the silicon photomultiplier. Preferably, the overvoltage is under 3 volt. Preferably, the overvoltage is 1.5 volt.

In some embodiments, the controller adjusts the reverse bias voltage applied on the silicon photomultiplier according to different operation modes to control the overvoltage.

In some embodiments, the sample analyzer includes a temperature control device for controlling a temperature of the silicon photomultiplier at a configuration temperature. Preferably, the configuration temperature is selected between 20° C. to 40° C. Preferably, the configuration temperature is selected between 25° C. to 35° C.

In some embodiments, the sample analyzer includes a temperature compensation device for adjusting a reverse bias voltage applied on the silicon photomultiplier according to a temperature of the silicon photomultiplier so as to keep an overvoltage constant. The temperature compensation device comprises a temperature sensor, a temperature detection circuit, an AD converter, a temperature compensation module, a DA converter, a voltage adjustment circuit and a regulation power supply with an adjustable output, wherein the temperature sensor and the temperature detection circuit detect the temperature of the silicon photomultiplier and generate a temperature signal, the AD converter converters the temperature signal into a digital signal, the temperature compensation module calculates a target value of the reverse bias voltage of the silicon photomultiplier, the controller adjusts a circuit parameter of the voltage adjustment circuit by controlling the DA converter to cause an output voltage of the adjustable regulation power supply to reach the target value of the reverse bias voltage.

In some embodiments, a sample analysis method for a sample analyzer of the embodiments of this application includes: providing an analyte comprising cell particles treated with a reagent; providing an optical measurement device comprising a fluid chamber, a light source and a light detector comprising at least one silicon photomultiplier; when the analyte flows through the fluid chamber and forms a sample stream, illuminating the sample stream flowing through the fluid chamber by the light source to generate a light signal, and transforming the light signal into light signal information after the light detector receives the light signal; and classifying the cell particles according to the light signal information.

In some embodiments, the cell particles are at least selected from red blood cells, white blood cells and platelets.

In some embodiments, the light power of the light source is between 5 to 15 mW.

In some embodiments, the silicon photomultiplier includes a plurality of light sensing units arranged in an array configuration, an illumination area of each light sensing unit is smaller than an imaging area of a single cell particle.

In some embodiments, the reverse bias voltage applied on the light sensing units is larger than a breakdown voltage.

In some embodiments, a first reverse bias voltage is applied on the light sensing units when the cell particles are white blood cells and a second reverse bias voltage is applied on the light sensing unit when the cell particles are reticulocytes, the first reverse bias voltage is smaller than the second reverse bias voltage.

BRIEF DESCRIPTION OF THE DRAWINGS

For explaining embodiments of the present application or conventional technology more clearly, figures used for explaining embodiments or conventional backgcircle are shortly introduced below. Obviously, in the drawings, similar drawings contain similar symbols for the same device or part, or for a part which has an analogous function and/or analogous structure. It should be understood that these drawings describe different kinds of embodiments, but are not to be considered as limitations of the scope.

The left figure is the characteristic diagram for detecting lights with very weak fluxes (single photon level). The right figure is the characteristic diagram for detecting lights with higher power.

Figure 11:
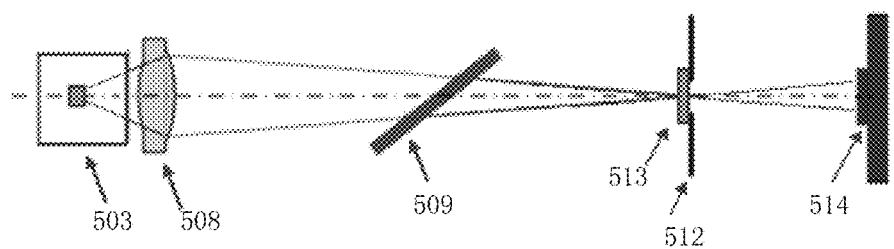

FIG. 11 is a portion of the optical path schematic of the optical measurement device for one embodiment of the present invention.

Figure 12:
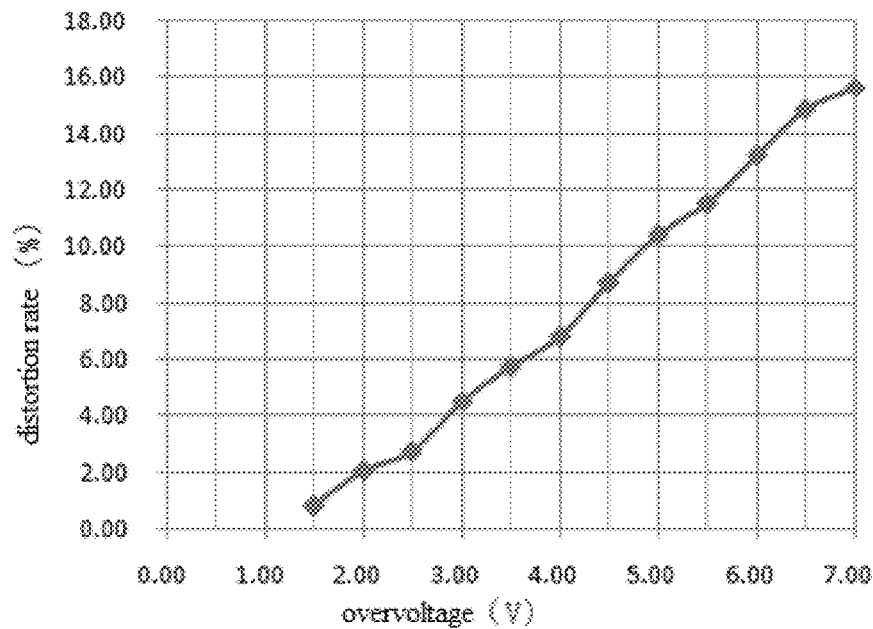

FIG. 12 is a voltage-varying characteristic curve diagram of the crosstalk rate of the silicon photomultiplier.

Figure 13:
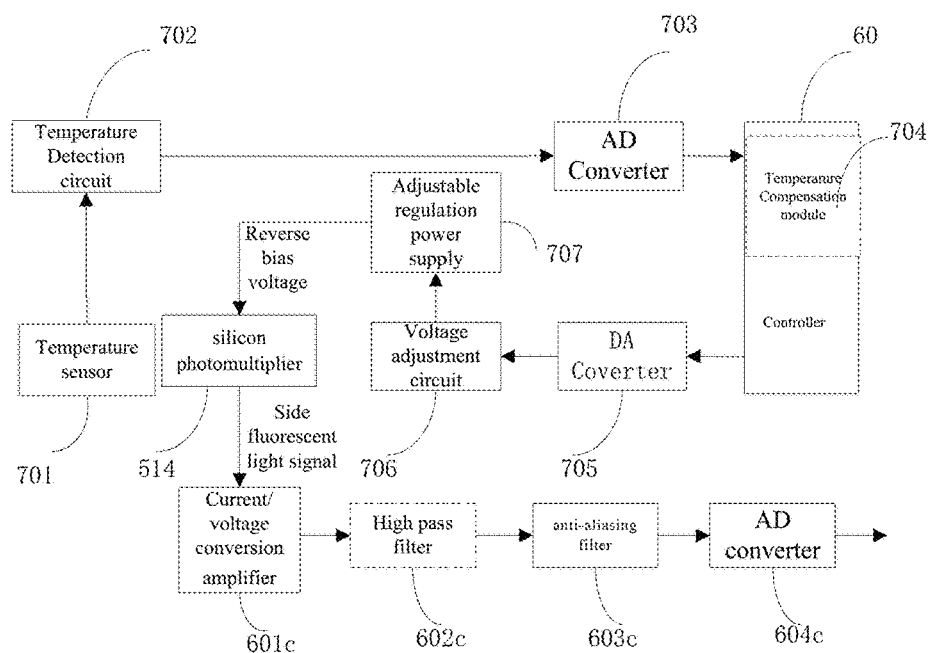

FIG. 13 is a portion of functional module schematic of the sample analyzer for one embodiment of the present invention.

Figure 14:
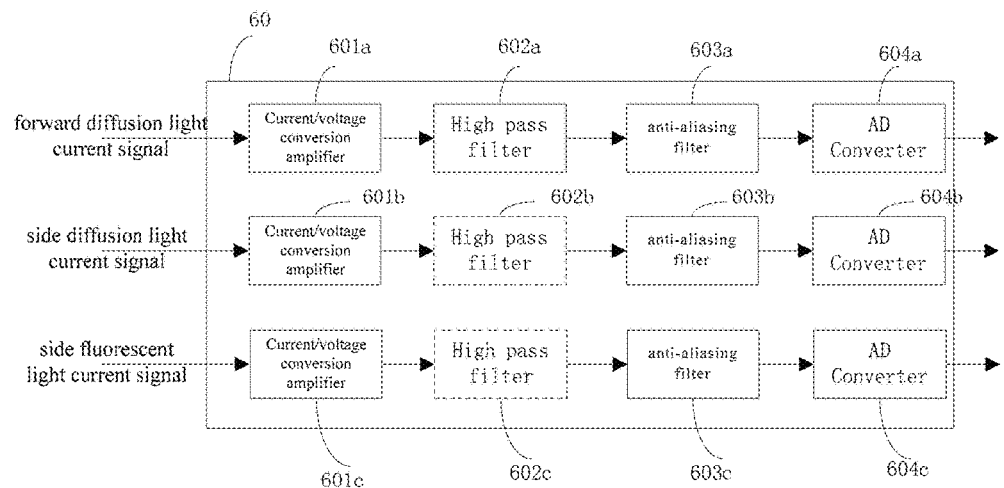

FIG. 14 is a portion of functional module schematic of a controller of the sample analyzer for one embodiment of the present invention.

Figure 15:
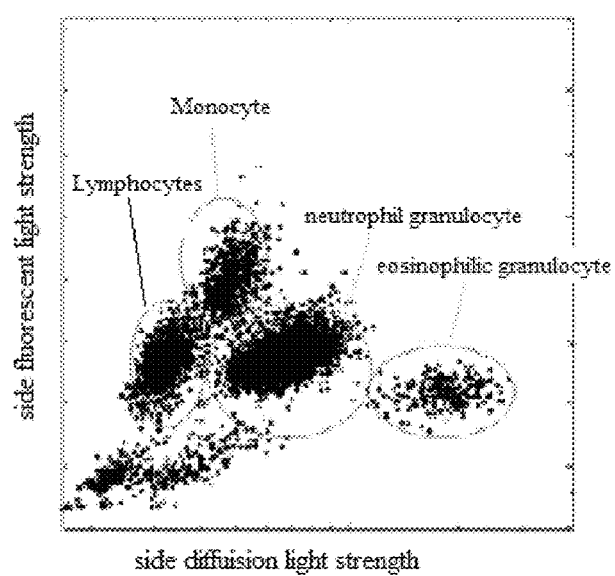

FIG. 15 is a scatter diagram of white blood cells in a regular analyte analyzed by the sample analyzer for one embodiment of the present invention.

Figure 16:
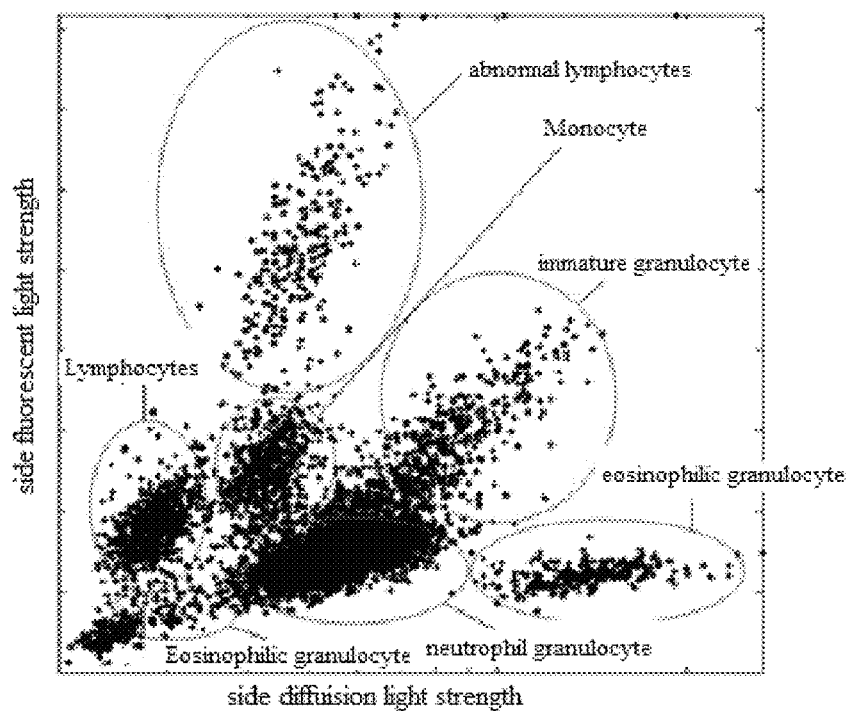

FIG. 16 is a scatter diagram of white blood cells in an abnormal analyte analyzed by the sample analyzer for one embodiment of the present invention.

Figure 17:
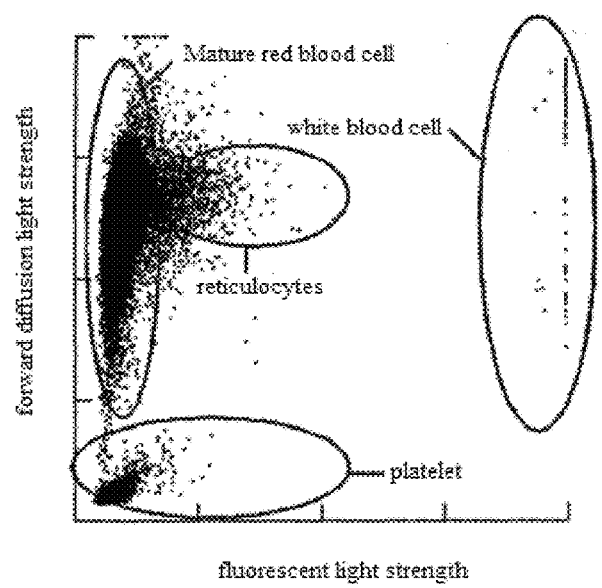

FIG. 17 is a scatter diagram of reticulocytes analyzed by the sample analyzer for one embodiment of the present invention.

Figure 18:
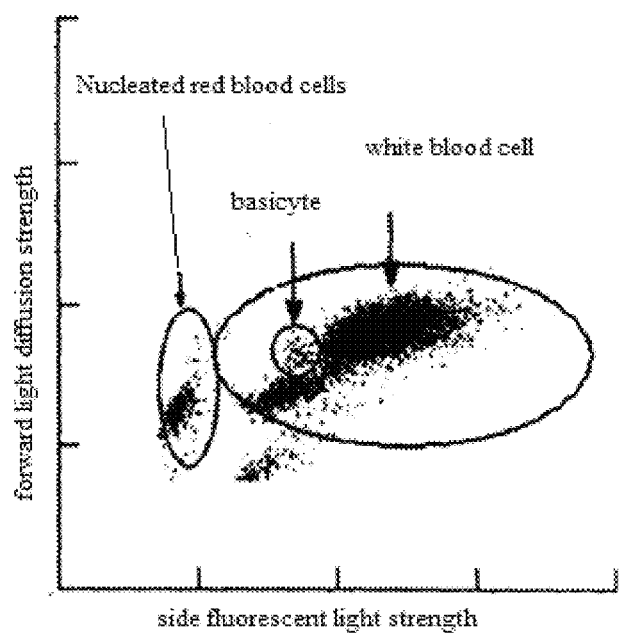

FIG. 18 is a scatter diagram of nucleated red cells of the sample analyzer for one embodiment of the present invention.

DETAILED DESCRIPTION

Specific details for fully understanding each of embodiments and implemented by the skilled in the art are provided in bellow description. However, it should be understood for those skilled in the art that the present invention is able to be implemented without the specific details as well. In some embodiments, conventional structures and functions are omitted to avoid confusions in the descriptions of the embodiments.

Unless it is acquired clearly under context of the descriptions, the terms "comprise", "include" should be defined as opening definition but not limited or exhaustive definition.

According to the research for the sensitivity of the avalanche photodiode when it operates as a fluorescent light detector, it is found that the sensitivity for detecting fluorescent lights of an avalanche photodiode can be increased by several approaches listed below:

(1) controlling the area range of light sensor of the avalanche photodiode, for instance, controlling the diameter or length of the light sensor in the range between 0.1-2 mm.

However, by doing so, the specification requirement of an auxiliary optical path for the fluorescent light detector would be raised. For example, convergence lens should be implemented by special specification aspheric lens under above condition.

In addition, the auxiliary optical path will become very sensitive and hard to be adjusted. Moreover, the specification requirement for the controller of the light detector would be raised as well. Such as, a proper low-pass filter, a proper high-pass filter and a proper baseband adjustor would need to be configured between the electrode capacitors of the avalanche photodiode, which cause the controller of the fluorescent light detector to become more complicated.

Moreover, requirements for the control circuit of the light detector will become higher. For instance, a proper low pass filter, a high pass filter and a baseband adjustor are required to be configured according to the electrode capacitor of the avalanche photodiode. The control circuit of the fluorescent detector will become more complicated correspondingly.

(2) Increasing power of the light source of the sample analyzer

If the avalanche photodiode is implemented as the fluorescent light detector, for increasing sensitivity of the fluorescent light detector, a laser generator with 20 mW or a 25 mW power should be applied as the light source. On the contrary, only 5 mW power laser generator is needed when the vacuum photomultiplier is implemented as the fluorescent light detector. A light source with higher power would significantly increase cost, for example, if power of the light source needs to be double, the cost of it is double as well accordingly.

(3) Increasing the circuit gain of the avalanche photodiode

For example, the circuit gain of the vacuum photomultiplier is generally between 10-100 KV/A, bur for generating output signals with the same amplitude as the vacuum photomultiplier generating, the circuit gain of the vacuum photomultiplier needs to be increased to reach 1-50MV/A. It would cause the noise rate of the fluorescent signals detected by the avalanche photodiode to be 50% higher than the noise rate detected by the vacuum photomultiplier. For instance, the fluorescent light detector implemented by the vacuum photomultiplier is able to control the noise rate under 150 mVpp, thus, under the condition that the range of an A/D converter is 4 volt, noise is about to less than 4% of the detection signals. Instead, if the avalanche photodiode is implemented and the sensitivity of it is increased by the gain circuit, it would be hard to control the noise of the fluorescent signals to be controlled under 300 mVpp.

Increase of noise could cause negative effects on 5 classes classification of white blood cell. More seriously, it would influence the sensitivity for detecting abnormal cells and further affect the abilities for alarming when abnormal analyte appears. For example, in the detection of immature granulocytes, although immature granulocytes distribute on upon of the neutrophils on the direction of side fluorescent light strength in the scatter diagram of the classification of white blood cell, there is no significant interval between neutrophils group and immature granulocytes group. Since the neutrophils take 50%-70% in all white blood cells, far greater than the percentage of immature granulocytes, it would be easy to misjudge neutrophils as immature granulocytes when noise of the fluorescent signals is louder and vice versa. Louder the noise is, probability for negative or positive misjudges is increased.

In addition, amounts of mature red blood cells are far more greater than amounts of reticulocytes. (amounts of RBC for a regular adult is approximately between $3.5\text{-}5.5\times10^{12}$/L, and amounts of reticulocytes is only between $0.02\text{-}0.2\times10^{12}$/L, which is 0.5%-1.5% of RBC)

Therefore, boundaries between groups of reticulocytes and RBC would be blurred in the scatter diagram of reticulocytes detected by the avalanche photodiode. It would be easy to misjudge RBC as reticulocytes and vice versa when noise of the fluorescent signals is louder. The sensitivity for detecting abnormal cells and the abilities for alarming when abnormal analyte appears would go down correspondingly. In the mean time, the detection circuit is complicated and it's difficult to adjust the optical path.

It is found in the research additionally, only above three ways are applied at the same time will make the avalanche photodiode to satisfy the requirement of fluorescent light detector. Therefore, noise issues are hard to overcome when the avalanche photodiode is operated as a light detector for fluorescent lights detection. The sensitivity for detecting abnormal cells and the abilities for alarming when abnormal analyte appears would go down correspondingly. In the mean time, the detection circuit is complicated and it's difficult to adjust the optical path.

Figure 1:
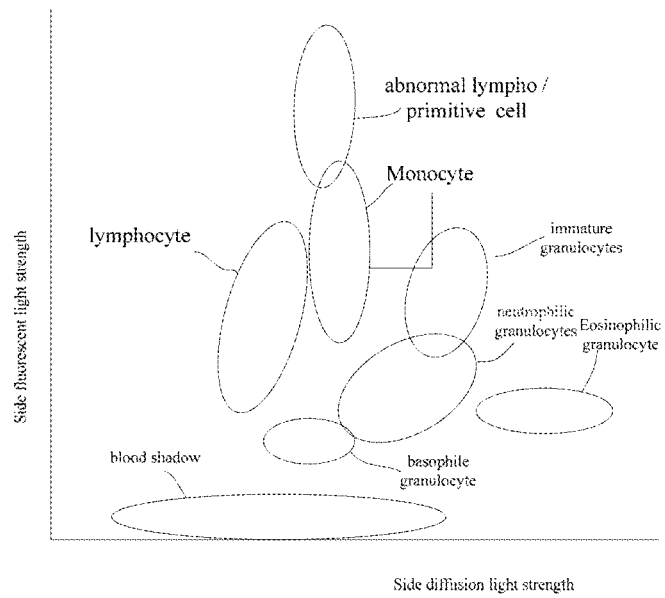
FIG. 1 is a scatter diagram of white blood cell classification.
Figure 2:
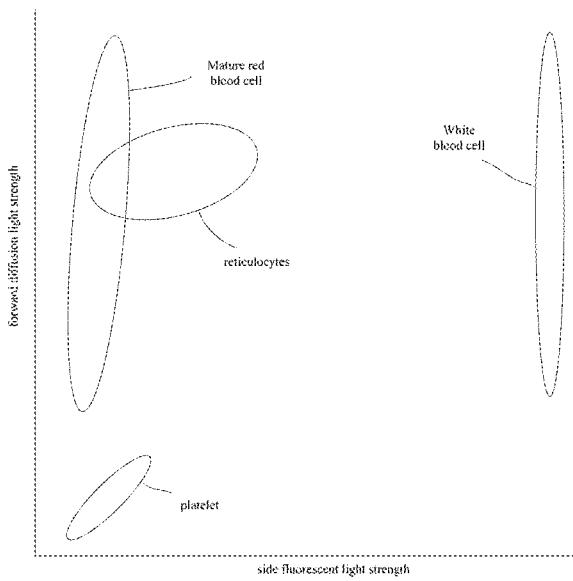
FIG. 2 is a scatter diagram of reticulocytes.
Figure 3:
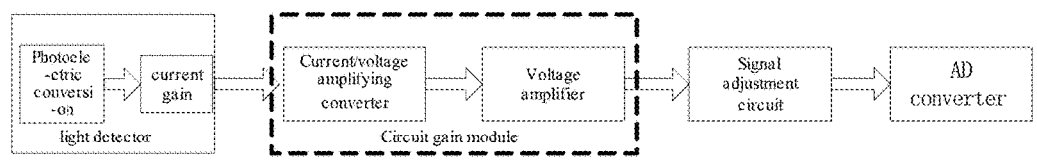
FIG. 3 is a functional module schematic of a fluorescent light detection circuit.
Figure 4:
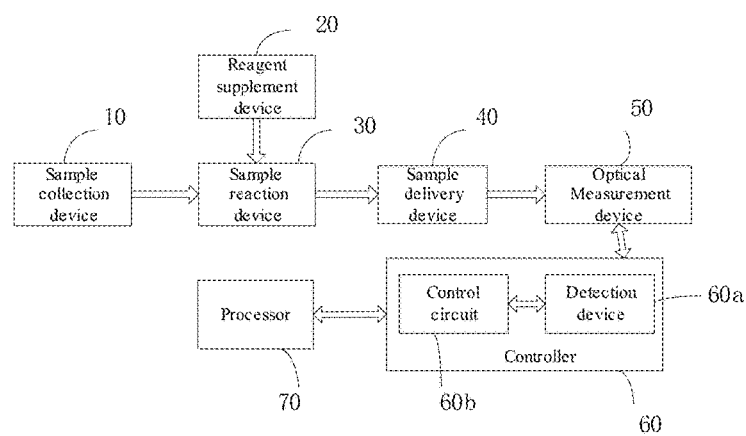
FIG. 4 is a functional module schematic of a sample analyzer for one embodiment of the present invention.

Please refers to FIG. 4, a sample collection device 10, a reagent supplement device 20, a sample reaction device 30, an analyte delivery device 40, an optical measurement device 50, a controller 60 and a processor 70 are disclosed.

The sample collection device 10 is implemented for quantitatively collecting a sample and delivering the sample to the sample reaction device 30. In some embodiments, the sample collection device 10 includes a sampling needle, an injector and a clean swab for cleaning the sampling needle (not shown in FIGs). Obviously, the sample collection device 10 is not limited to be implemented under above disclosures but is able to be configured according to requirements. For instance, in some other embodiments, the sample collection device 10 could further include an autoloader, a compartment, a sample rotary valve and a metering pump (not shown in FIGs).

The reagent supplement device 20 is implemented for collecting a ration reagent from a reagent tube or a reagent bin and delivering the ration reagent to the sample reaction device 30. In some embodiments, the reagent includes diluents, fluorescent dye and/or hemolytic agent. The reagent is able to be configured according to the configuration of measurement models. If only white blood cell classification model is conducted, the reagent should include diluents, a hemolytic agent capable of lysing red blood cells and morphological processing white blood cells and a fluorescent dye only for white blood cell dying. If only reticulocytes counting model is conducted, the reagent should include diluents, a hemolytic agent capable of conducting morphological processing for red blood cells and a fluorescent dye only for reticulocytes dying.

In some embodiments, the reagent supplement device 20 includes an injector and necessary pipeline clean device. Obviously, the reagent supplement device 20 is not limited to be implemented under above disclosures, but is able to be properly adjusted according to specific requirement. Such as, in other embodiments, the reagent supplement device 20 could include a metering pump or a liquid storage pool for storing multiple reagents.

The sample reaction device 30 is implemented for containing the sample and the reagent to make the sample and the reagent to react for generating the analyte. In some embodiments, the sample reaction device 30 could include a temperature control device and a blending device. The temperature control device is implemented for providing a proper temperature environment to the reaction between the sample and the reagent. 42° C. is selected in some embodiments. Obviously, the temperature environment should be selected under requirements but not limited in above discussed embodiments.

The blending device is implemented for sufficiently blending the sample and the reagent. In some embodiments, the blending device, including an air pump and a control valve, could be implemented by generating bubbles to blend the sample and the reagent. It should be noted that the blending device could be implemented under other proper configuration in other embodiments but not limited to embodiments disclosed above. For example, the blending device, including an electrical mechanism, could be implemented by electric machinery for blending the sample and the reagent.

It should be understood that the entire sample reaction device 30 should be configured under practical requirements in other requirements but not limited to above embodiments. For instance, if reaction ability of the reagent is enough, the temperature control device and the blending device of the sample reaction device 30 could be omitted. In addition, multiple sample reaction modules respectively selected as the sample reaction device 30 in different measurement models is acceptable. For example, the white blood cell classification and the reticulocytes classification generally are conducted with different sample reaction modules. That could increase detection performance firstly, and avoid cross pollutions among different measurement models secondly.

The analyte delivery device 40 is implemented for delivering the analyte into the optical measurement device 50. Specifically, the analyte delivery device 40 delivers the analyte sufficiently reacted to the optical measurement device 50. In some embodiments, the analyte delivery device 40 could include two injectors, a pipeline and a control valve. One of the injector is implemented for driving the analyte passing through the optical measurement device 50 via the pipeline. Specifically, one of the injector provides pressures to make the analyte passing through the optical measurement device 50 and the other injector is implemented for driving diluents to form sheath fluid. The sheath fluid wraps up the analyte so as to form a sample stream passing through the optical measurement device 50.

The control valve could be configured on the pipeline for controlling on/off of the pipeline between different sample reaction devices to the optical measurement device 50 so as to select a proper analyte into the optical measurement device 50.

It should be understood that the analyte delivery device 40 should be configured under practical requirements in other requirements but not limited to above embodiments. Specifically, the injector could be replaced by an air source generating pressures or a liquid tank driving by pressures.

The optical measurement device 50 is implemented for illuminating the sample stream, collecting diffusion lights and fluorescent lights of cell articles when cell articles are illuminated and outputting corresponding electrical signals (diffusion light signal and fluorescent lights signals) of diffusion lights and fluorescent lights. In this embodiment, the electrical signals respectively reflect strength of the light signals (diffusion lights and fluorescent lights) so that electrical signals also can be defined as light signal information.

Figure 5:
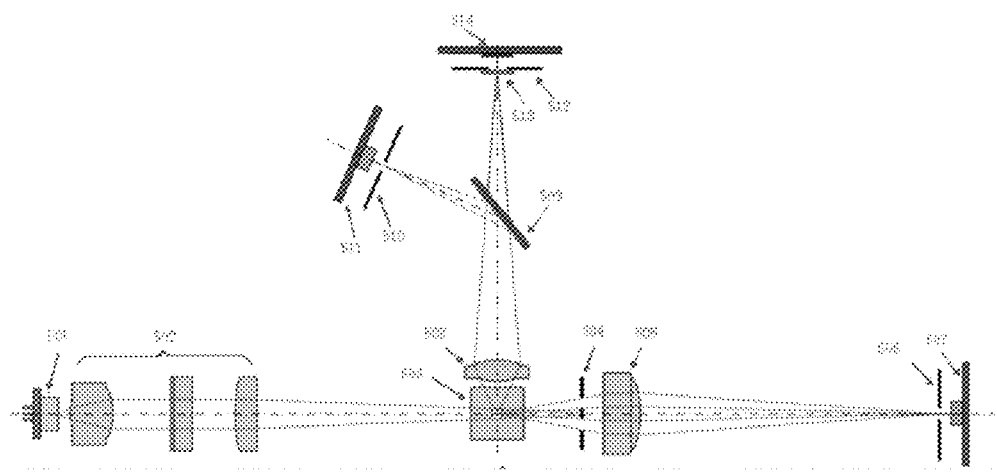
FIG. 5 is an optical path schematic of the optical measurement device of the sample analyzer for one embodiment of the present invention.
Figure 6:
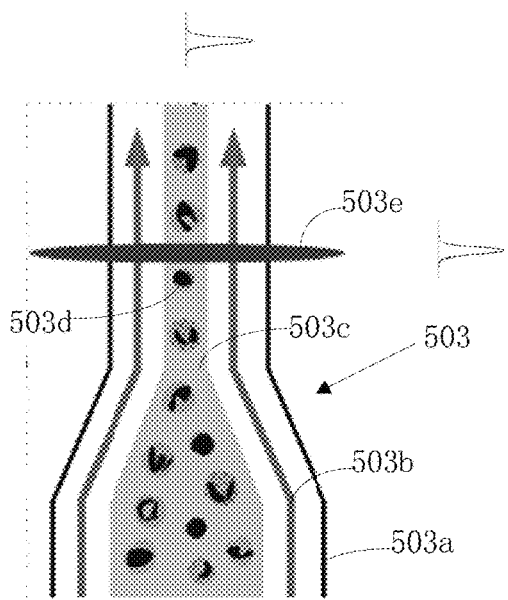
FIG. 6 is a fluid chamber schematic of the optical measurement device for one embodiment of the present invention.

The optical measurement device. Please refers to FIG. 5, in some embodiments, the optical measurement device 50 includes a light source 501, an irradiation lens group 502, a fluid chamber 503, a first aperture 504, a first converging lens 505, a second aperture 506, a first light detector 507, a second converging lens 508, a dichroic mirror 509, a third aperture 510, a second light detector 511, a fourth aperture 512, a longpass filter 513 and a third light detector 514.

In some embodiments, light source 501 could be implemented by a laser generator, such as a laser diode with 635 nm operation wavelength. It should be understood that the light source 501 should be configured under practical requirements in other requirements but not limited to above embodiments.

In other word, flow cytometry are applied to the sample analyzer for cells classification and cells count. Of course, implementation of the fluid chamber 503 is not limited to above embodiments. Alternatives could also be applied in other embodiments for the requirements of measurement.

In some embodiments, the irradiation lens group 502 is configured on the light path between the light source 501 and the fluid chamber 503. The irradiation lens group 502 is applied for converging lasers generated by the light source 501 to form a proper facula illuminating the illumination zone 503e. The facula focus on the cell articles 503d in the sample stream 503c to generate diffusion lights and fluorescent lights.

Wherein, the diffusion lights includes forward low angle scattering lights with 1-10 degrees angle compared to the optical axis and side scattering lights basically vertical with the optical axis. The forward low angle scattering lights refers to the volume of the cell articles 503d. The side scattering lights refers to the complexity of inside structure of the cell articles 503d. The fluorescent lights include side fluorescence basically vertical with the optical axis. The side fluorescence refers to the content of DNA and RNA in the cell articles 503d.

Intensity of the forward low angle scattering lights is strongest. Intensity of the side scattering lights is less than it of the forward low angle scattering lights. Intensity of the side fluorescence is much less than it of the forward low angles scattering lights and the side scattering lights. In some embodiments, the irradiation lens group 502 includes collimating lens and cylindrical lens.

In some embodiments, the irradiation lens group 502 includes collimating lens and cylindrical lens. Of course, implementation of the irradiation lens group 502 is not limited to above embodiments. Alternatives could also be applied in other embodiments for the requirements of measurement.

The first converging lens 505 is configured on the optical axis of the light source 501 and located at the other side of the fluid chamber 503 for collecting the forward low angle scattering lights. The first aperture 504 is configured on the first converging lens 505 for blocking direct lights. The first light detector 507 is configured on a converging light path of the first converging lens 505, such as on a converging spot, for collecting the forward low angle scattering lights and transforming it as a corresponding electrical signal (forward scattering light signal). The second aperture 506 is configured in the front of the first light detector 507 for removing environment lights.

It is understood that an auxiliary light path of the first light detector 507 is constructed of the first aperture 504, the first converging lens 505 and the second aperture 506, which is applied for increasing the detection performance and the signal noise rate of the first light detector 507.

For certain, implementation of the auxiliary light path of the first light detector 507 is not limited to above embodiments, alternatives could also be applied in other embodiments for the requirements of measurement.

The second converging lens 508 is configured on a light path basically vertical with the fluid chamber 503 and the light source 501 for collecting the side scattering lights and the side fluorescent lights. The dichroic mirror 509 is configured on the converging light path of the second converging lens 508 for separating the side scattering lights and the side fluorescent lights. The second light detector 511 is configured on the light path of the side scattering lights of the dichroic mirror 509, such as located on the converging spot, for collecting side scattering lights and transforming it as a corresponding electrical signal (side scattering light signal). The third aperture 510 is configured in the front of the second light detector 511 for removing the environment lights. The third light detector 514 is configured on the light path of the side fluorescent lights of the dichroic mirror 509, such as located on the converging spot, for collecting the side fluorescent lights and transforming it as a corresponding electrical signal (fluorescent light signal or side fluorescent light signal). The long pass filter 513 and the fourth aperture 512 are both configured in the front of the third light detector 514 in sequence for removing stray lights in the light path and environment stray lights other than fluorescent light wavelength.

It is understood that an auxiliary light path of the second light detector 511 and the third light detector 514 is constructed of the second converging lens 508, the dichroic mirror 509, the third aperture 510, the long pass filter 513 and the fourth aperture 512. The auxiliary light path is applied for increasing the detection performance and the signal noise rate.

For certain, implementation of the auxiliary light path of the second light detector 511 and the third light detector 514 is not limited to above embodiments, alternatives could also be applied in other embodiments for the requirements of measurement. It should be noted that in some other embodiments, some elements of the optical detection device 50 could be omitted, such as the second aperture 506.

For some embodiments, in the consideration of the condition that forward scattering lights and side scattering lights are relative stronger, sensitivity of the PIN photodiode is enough to satisfy with the requirements for measuring. Therefore, the first light detector 507 and the second light detector 511 are able to be implemented by applying low cost PIN photodiode so as to cut down the cost of the sample analyzer.

Since the intensity of the side fluorescent lights is much less than that of the forward scattering lights and the side scattering lights, disadvantages of large volume and high cost are raised if vacuum photomultiplier is implemented. On the other hand, although cost is cut down, the disadvantage of lack of enough sensitivity is also raised when the avalanche photodiode is implemented.

Figure 7:
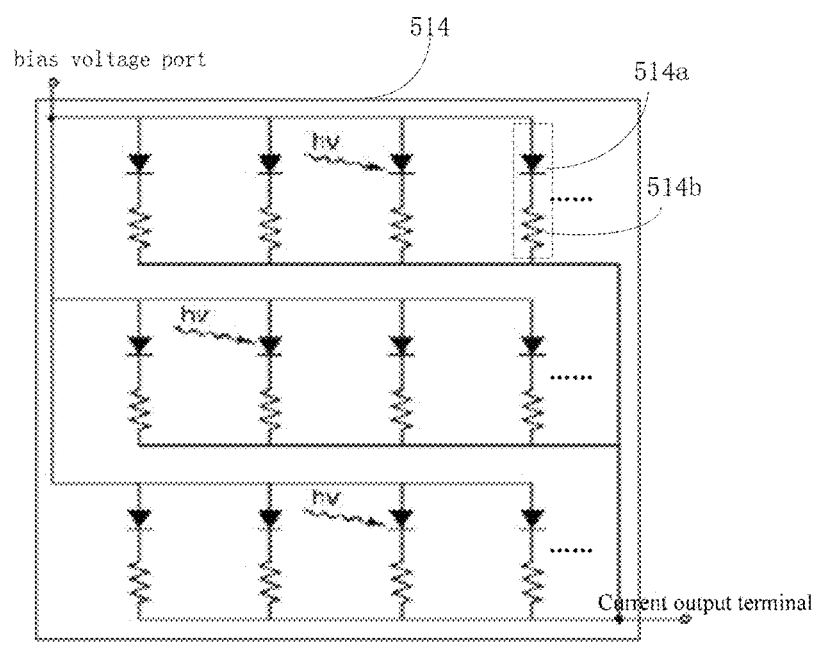
FIG. 7 is a structure schematic of a silicon photomultiplier for one embodiment of the present invention.

Please refers to FIG. 7, the third detector 514 includes a planar array consisting of multiple light sensors. Each light sensor includes a micro element of light sensing diode 514a and a quench resistor 514b connecting in series with each other. The size of the light sensor is between several microns to hundreds of micron. The amount of the light sensors should be between hundreds to ten-thousands. The resistance of the quench resistor 514b is normally between several hundred Ohms to mega-ohms.

The silicon photomultiplier is with advantages of small volume, high sensitivity (gain is high to reach $10^6$, which is close to the gain of vacuum photomultiplier), low operation voltage (generally dozens of volts), low cost (less than $\frac{1}{10}$ of vacuum photomultiplier, almost equal to avalanche photodiode) and low sensitivity for magnetic field.

Therefore, silicon photomultiplier is applied to implement as the third light detector 514 so as to make the optical detection device 50 and the sample analyzer having advantages of high sensitivity, high signal noise rate, small volume and low cost.

Figure 8:
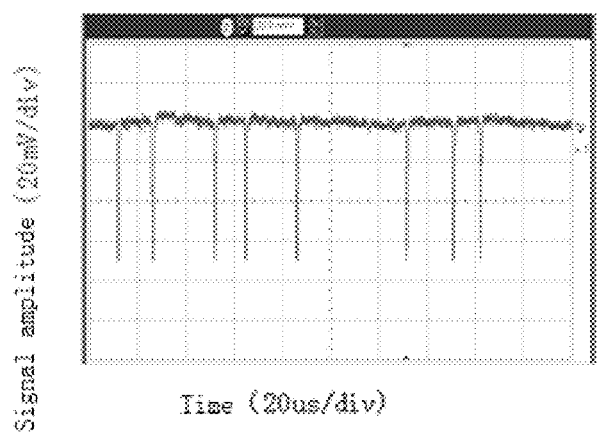
FIG. 8 is an output signal characteristic diagram of single/multiple photons detected by photosensitive units of the silicon photomultiplier.

Please refers to FIG. 8 as well, each of light sensor operates under the Geiger-mode. For example, when a reverse bias voltage over the breakdown voltage of the micro unit of the light sensing diode 514a is applied on the light sensor, the current passing through the light sensing diode 514a would increase significantly. However, since there is quench resistors 514b in this light sensor, when voltage drop generated from the quench resistor grows, it causes the reverse bias voltage on the light sensing diode 514a to become smaller than the breakdown voltage. Therefore, current amplifying effect ends and the outputting mode of the light sensing diode 514a turns back to its initial state, which is a mode for outputting current impulses with fixed range. In this process, current gain could reach $10^5$-$10^6$, so that the light sensing diode is workable to be applied for single photon detection.

Light detector unit is operated as a photon trigger. Output signal (current) of it only has two state "0" or "1". In its state "1", amplitude of the output signal is not relative with the number of emitting photons but fixed. It means no matter how much photon emit to the light sensor unit in the meantime, the output signal is basically fixed with a constant amplitude the same as only one photon emits to the light sensor unit.

Figure 9:
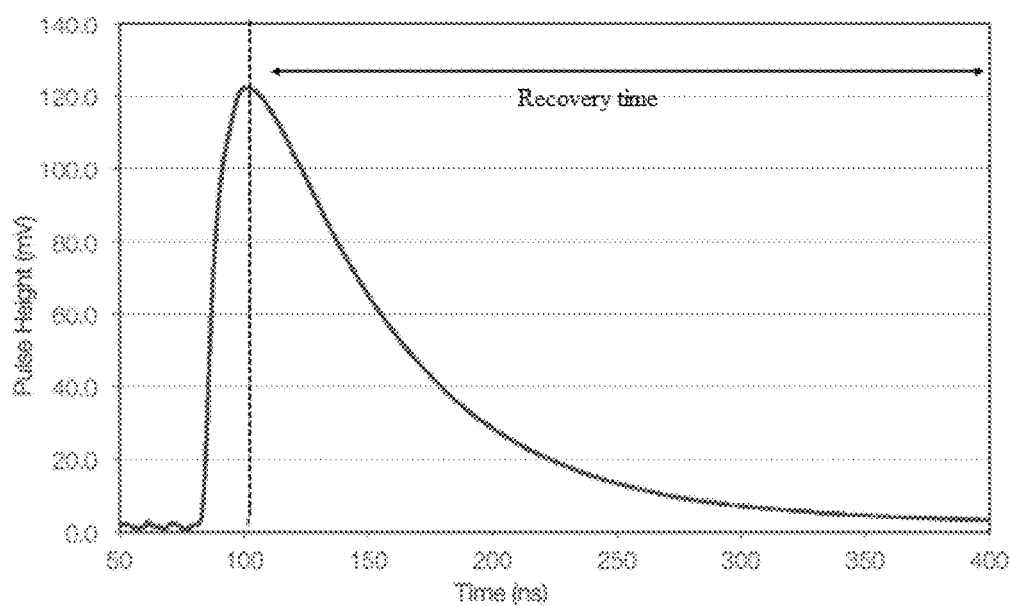
FIG. 9 is a time-varying characteristic curve diagram of the output signal of a photosensitive unit.

Please refers to FIG. 9, another feature of output signal of the light sensor unit is shown. After photons are detected, the output signal would reach the fixed maximum value in very short time (usually during few nanoseconds) then starts to decay and returns to zero. Decaying time of above is defined as recovery time, as well as dead zone time, usually with hundreds nanoseconds. In this recovery time, even next photon reaches to the light sensor unit, there is no any signal outputted from the light sensor at all. Only after the recovery time, next detection period for detecting photons could be conducted.

Figure 10:
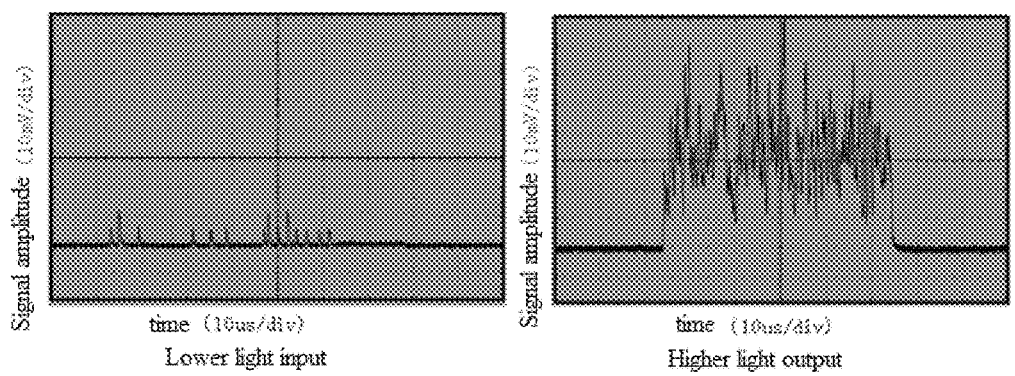
FIG. 10 is an output signal characteristic diagram of lights with different fluxes detected by the silicon photomultiplier.

Detection methods for detecting fluorescent lights among silicon photomultiplier, light sensor unit and avalanche photodiode are totally different. The avalanche photodiode must operate on linear mode to transform different light strengths into electrical signals with different strengths when it is applied to detect fluorescent lights. In the other word, reverse bias voltage should be configured under breakdown voltage to detect fluorescent lights so that the amplitude of the output signal is proportional to the strength of input light. However, under linear mode, the maximum current gain is generally between dozens or hundreds times. On the contrary, when the silicon photomultiplier disclosed in this application is applied to detect fluorescent lights, each of the light sensor unit works at the Geiger-mode, in which the amplitude of the output signal for a single light sensor unit is basically a fixed value, would not increase corresponding to the increase of the strength of input lights. The advantage of above is that the maximum current gain under the Geiger-mode can reach $10^5$-$10^6$ so that the sensitivity of the silicon photomultiplier can stand on a very high level. The silicon photomultiplier of the present application consists of light sensor units array, in which the area of single light sensor unit is much less than the area of fluorescent facula. In the other word, the area of single light sensor unit is less than the area of imaging for a single cell article. In ideal condition, the single light sensor would receive the illumination of single photon to generate an electrical signal for a single photon. As shown in FIG. 10, since large numbers and high density of light sensor units are integrated as the silicon photomultiplier, the output of the silicon photomultiplier in an unit time is the output sum of all of the light sensors. Therefore, the silicon photomultiplier disclosed in this application is able to transform lights with different strengths into electrical signals with different strengths and with very high sensitivity as well.

The Controller

Please refers to FIG. 4, FIG. 13 and FIG. 14 at the same time, the controller 60 includes a measurement circuit 60a and a control circuit 60b. In some embodiments, the measurement circuit 60a includes a current-voltage transformation amplifier 601c, a high-pass filter 602c, an anti-aliasing filter 603c and AD converter 604c. The current-voltage transformation amplifier 601c could configure the circuit gain for the third light detector 514 (the silicon photomultiplier).

Besides above current-voltage transformation amplifier 601c, a high-pass filter 602c, an anti-aliasing filter 603c and AD converter 604c, the measurement circuit 60a further includes current-voltage transformation amplifiers 601a and 601b, high-pass filters 602a and 602b, anti-aliasing filters 603a and 603b and AD converter 604a and 604b.

Electrical signals outputted from the first light detector 507, the second light detector 511 and the third light detector 514 pass through the current-voltage transformation amplifiers 601a, 601b and 601c to conduct current/voltage transformation and respectively transmit into the AD converters 604a, 604b and 604c after signal processing to transform the electrical signals into digital signals in favor of the process of the processor 70.

It means current-voltage transformation amplifiers 601a, 601b and 601c are respectively applied for transforming current signals outputted from the first light detector 507, the second light detector 511 and the third light detector 514 into voltage signals.

Regarding to forward scattering light signals, a signal processing circuit usually includes the high-pass filter 602a with lower cut-off frequency. It is useful for filtering direct light signals and eliminating baseline fluctuation in low frequency. However, different from using avalanche photodiode for detecting fluorescent lights and side scattering lights, the sample analyzer of this application using silicon photomultiplier as the light detector. For detecting side scattering light signals and fluorescent light signals, the high-pass filter 602b and 602c are not necessary since the baseline fluctuation of the high-pass filter 602b and 602c can be omitted. Therefore, the high-pass filter 602b and 602c can be omitted in some embodiments.

Base on general design principle, before the electrical signals are transmitted into the AD converter 604a, 604b and 604c, preferably, electrical signals should be processed by anti-aliasing filters 603a, 603b and 603c at first. Purpose of above preference is to prevent the high frequency portion of signals to be converted as part of low frequency interference overlapping with useful signals in the sampling process.

In addition, in some other embodiments, the measurement circuit 60a is configured after the current-voltage transformation amplifiers 601a, 601b and 601c, including a voltage amplifier with adjustable gain, for implementing the purpose of calibrating scatter diagram position.

In some other embodiments, calibration of the scatter diagram position is implemented by configuring a digital amplifier in the processor 70. The control circuit 60b is applied for controlling and driving relative portions about electromechanical elements, fluid path and temperature controller of the sample collection device 10, the reagent supplement device 20, the sample reaction device 30 and the analyte delivery device 40 to finish the detection operation. The processor 70 is applied for processing the digital signals outputted from AD converter 604a, 604b and 604c to get a test result.

It should be understood by skilled in the art that the control circuit 60b and the processor 70 could be integrated as a single controller, which could be implemented by a microcontroller unit. Above individual descriptions of this application for the control circuit 60b and the processor 70 are only disclosed for clear explanation, but not limitations of this application.

Please refers to FIG. 15, above disclosed sample analyzer could classify lymphocytes, monocytes, eosinophils, and neutrophils to achieving 4 classes of white blood cells. After disposing the sample by other reagent and classifying and amounting eosinophils through intensity information of forward scattering lights and intensity information of side scattering lights, the result of the 4 classes for white blood cells is combined with the result of eosinophils to realize a result of 5 classes for white blood cells.

Moreover, it is found in the research and development stage that, under ideal circumstance, if the number of incident photons is less than the number of light sensor units of the silicon photomultiplier and is distributed on the illumination zone on average, the current impulse amplitude for the output signal of the silicon photomultiplier would be linearly relative with the instant power of incident lights well. But, if the number of effect incident photons is greater than the number of light sensor units of the silicon photomultiplier or incident photons over concentrate on a few of light sensor units of the silicon photomultiplier, too many photons will emit on the same light sensor unit at the same time, the relation between the current impulse amplitude for the output signal of the silicon photomultiplier and the instant power of incident lights would not remain linearity.

For the sample analyzer, when linearity of the fluorescent signal is not enough, gaps among different cell clusters will get narrower in the scatter diagram. For example, in the white blood cell classification scatter diagram, fluorescent signals with bad linearity could cause lack of distinction between monocytes and neutrophils so as to influence the measurement result and warning sensitivity of the sample analyzer in the end. In the meantime, lack of linearity would cause the dynamic range of measurement to become insufficient as well.

For resolving issues relating to lack of linearity or dynamic range, by research, above issues could be resolved from two approaches: increasing the number of light sensor units of the silicon photomultiplier and reducing the number of photons emitting on single light sensor unit at the same time, which can also be defined as reducing luminous power on single unit area. Above ways are disclosed hereafter respectively:

Approach one: increasing the number of light sensor units of the silicon photomultiplier. In one embodiment of this application, the number of the light sensor units on the light detector is optimized.

As described above, the reason of lack of linearity could be that too many photons emit on the same light sensor unit at the same time so as to cause the output signal of the light sensor unit in this circumstance equals to the output signal outputted when only a photon emit on light sensor unit. For resolving that, by increasing the number of light sensor units in single unit area, the probability that multiple photons falls on the same light sensor unit should reduce. Calculation for the number of the light sensor units is described below:

Relation between the power of the incident light and the number of emitting photons is listed below:

$$Pt=NE=Nhc/\lambda$$

Wherein, P is the power of incident light, t is time, N is the number of incident photons in time period t, E is the energy of single photon, $h=6.63\times10^{-34}$, which is Planck constant, $c=3\times10^8$ m/s, which is light speed, $\lambda$ is wavelength.

In some embodiments, the laser emitted from the light source 501 is with 635 nm wavelength. The wavelength of exciting fluorescent lights $\lambda=670$ nm. Therefore, $E=2.97\times 10^{-19}$ J.

The width of fluorescent light pulse generated is 1 us when the cell article 503d passes through the illumination zone 503e and is illuminated. In this process, maximum number of incident photons instantly appears at the period t=100 ns of the top of the fluorescent light.

In some embodiments, the power of the light power is 5 mW, maximum instant power generated from the cell article 503d is about P=30 nW, but the photon detection efficiency of the silicon photomultiplier is only about 10% in the wavelength of 670 nm. It means only about 3 nW for 30 nW of maximum instant optical power is sensed effectively. The number of photons correspondingly sensed in above description is about N=Pt/E=1000.

Therefore, if the fluorescent facula is controlled to completely locate on the light sensing area of the silicon photomultiplier and each photon individually hits on different light sensing area of each light sensor units with no overlap, at least 1000 light sensing units are required. Moreover, since the sensing area of the silicon photomultiplier is usually formed as square but the fluorescent facula is usually circular or oval, the effectively utilizing area of the silicon photomultiplier would be 78% at most so that 1280 light sensing units are required at least.

However, design for the number of light sensor units of the silicon photomultiplier should not be limited to above disclosed embodiments. It should be understood that specific number of the light sensor units should be determined under practical requirements. For example, it should be determined according to the intensity of the fluorescent generated. If the intensity of the fluorescent lights is weaker, the number of the light sensor units needed is reduced. Otherwise, the number of the light sensor units is increased. For some certain embodiments, better linearity and dynamic range could be acquired if the number of the light sensor units is over 500.

In the embodiments of this application, the area of the light sensing unit is optimized. The area of the light sensing unit could properly be increased. Under above, it is no need to control the diameter or length of the light sensing unit to be maintained between 0.1-2 mm ranges.

In the condition that light sensing area of the silicon photomultiplier is under 1 mm$^2$, accuracy requirements for machining and assembling of auxiliary light path of the second light detector 511 and the third light detector 514 would become higher to make sure the fluorescent facula precisely falls within the light sensing area of the silicon photomultiplier. In the meantime, the light path would become very sensitive so as to make optical adjustment become harder, which would increase cost.

On the other hand, light sensing area of the silicon photomultiplier should be preferably less than a light sensing threshold area of the silicon photomultiplier. The light sensing threshold area is defined as a threshold area triggering a distortion of pulse amplitude of the fluorescent signal, the fluorescent signal is generated according to the amount of a dark pulse counts overlapping on single cell particle. In this embodiment, the light sensing threshold area is preferably less than 36 mm$^2$, because when the light sensing area of the silicon photomultiplier is more than 36 mm$^2$, the amount of dark pulse count of the silicon photomultiplier will increase significantly so as to cause the noise of the silicon photomultiplier raises accordingly.

In this embodiment, dark count is defined as the number of current pulse per second outputted from the silicon photomultiplier without light input. Dark count is caused by avalanche effect came from thermions of the light sensing diode 514a. Therefore, amplitude of current pulse for dark count is equal to amplitude of current pulse for a single photon. Dark count rate usually stays at 30 KCPS/mm$^2$ (KCPS is abbreviation for thousand units per second).

Larger the area of the silicon photomultiplier is, more dark count is generated accordingly. In the worst condition, dark count pulse will overlaps on the fluorescent signal pulse generated from the cell particle 503d so as to cause distortion of pulse amplitude. Less weak the fluorescent is, the effect of distortion is become worse. For the sample analyzer, width of the fluorescent light of the cell particle 503d is generally 1 us and the period of the fluorescent light of the cell particle 503d is at least 10 us. For limiting the effect of dark count, dark count pulse should be controlled to appear as less as possible in 0.3 us area on the top of fluorescent signal pulse, which requests the dark count rate should be controlled under 3.3 MCPS (MCPS is abbreviation for million counts per second). That means, light sensing area of the silicon photomultiplier should be less than 36 $mm^2$.

Therefore, reasonable area of light sensing area of the silicon photomultiplier is between 1-36 $mm^2$, shape of the light sensing area could be circular with diameter between 1.1-6.8 mm, such as circle with diameter between 2-6 mm. It could be a square with length between 1-6 mm or other shape with the same area, such as rectangle as well. In some embodiments, light sensing area of the silicon photomultiplier is shaped as a square with 3 mm length, which of area is 9 $mm^2$.

In one embodiment of this application, size for a single light sensing unit of the light detector is optimized. Size reduction of the single light sensing unit is helpful for increasing number of light sensing units in the silicon photomultiplier. Above number increase reduces the possibility of multiple photons reception in one single photon at the same time.

When light sensing area of the silicon photomultiplier is between 1-36 $mm^2$ and the number of the light sensing units is at least 1280, length of each light sensing unit should be less than 167 um as the silicon photomultiplier is shaped as square.

Concerning the recovery time for the light sensing unit after occurrence of the avalanche effect is positive correlative to capacitance value of the light sensing unit, it is understood that more the size of the light sensing unit is, equivalent capacitance growths correspondingly so as to extend the recovery time. Since the light sensing unit is with no function for detecting next photon during the recovery time and the side fluorescence generated by the sample analyzer is a multiple photons signal with sustained duration about 1 us, accordingly, number of photons unable to be detected by the light sensing unit would increase in quantity when the recovery time is getting longer so that linearity between photon numbers and outputting current is influenced relatively.

When the size of the light sensing unit is more than 50 um and the recovery time increases to be more than 500 ns, it means only two photons could be detected by each light sensing unit during the duration of fluorescence generated by a cell particle, which could influence the detection result significantly. Therefore, a proper size for the light sensing unit should be defined as 50 um or under 50 um, so as to control the recovery time below 300 ns.

However, size of the light sensing unit also relates to the current gain of the silicon photomultiplier. When the size of the light sensing unit is under 10 um, current gain would reduce to be fewer than $10^5$ accordingly. Therefore, the circuit gain of the silicon photomultiplier should be improved, which would cause noise increase in the mean time. That is not propitious for the silicon photomultiplier to get closer or better noise characteristic comparing with vacuum photomultiplier.

Therefore, proper size of the light sensing unit should be controlled between 10 um to 50 um as accurate as possible. In some embodiments, size of the light sensing unit is about 35 um.

In conclusion under above, light sensing area of the silicon photomultiplier could be controlled between 1-36 $mm^2$, size of the light sensing unit could be controlled between 10 um-50 um and the number of the light sensing unit could be controlled at 1280 units or above.

Approach two: reducing incident photons in one single light sensing unit at the same time. Or rather, reducing light power in unit area. In another embodiment of this application, light source power in the optical detection device is conducted optimization.

Because laser emitted from the light source 501 generates forward diffusion light side diffusion light and fluorescent light at the same time when the laser illuminates on the cell particle 503d, max power of the side diffusion light could probably reach 20 uW. As disclosed above, PIN type photodiode is implemented as the second light detector 511 to detect side diffusion light for reducing cost of the sample analyzer and the sensitivity of PIN type photodiode is about 0.4 A/W. Therefore, for requiring side diffusion light signal with proper amplitude, detection circuit gain of the PIN type photodiode is generally configured to be over 700 KV/A. In addition, circuit bandwidth should be remained over 500 KHz so that noise of PIN type photodiode could probably over 30 mVpp under this condition. The less the laser power is, the more noise of the detection circuit of PIN type photodiode become, which means the signal/noise rate gets worse accordingly. Worse signal/noise rate would influence the scatter diagram of white blood cells classification or the scatter diagram of reticulocytes significantly, so as to influence classification or counting of cells in the end. Therefore, in some embodiments, power of the light source 501 is preferably over 5 mW. Of course, in some other embodiments that the avalanche photodiode is implemented for detecting side diffusion light, power of laser could be controlled under 1 mW, but cost would increase accordingly for this implementation.

Therefore, light source over 1 mW could be applied as the light source of this application. In the comprehensive consideration of performance and cost, light source power limited under 20 mW is more preferable. Preferably, light source power between 5-15 mW is selected. Moreover, a proper light source power of above should be able operate between 5-15 mW and to be adjusted dynamically according to requirements.

In another embodiment of this application, optimization for the relationship between fluorescent facula and light sensing area of the optical detection device is conducted. If light power of the light source is remained steady, the number of incident photons illuminating on a single light sensing unit at the same time could be reduced by enlarging facula area of the side fluorescent light. On the other hand, for making facula of the side fluorescent light to cover the light sensing area of the silicon photomultiplier as large as possible, light sensing area of the silicon photomultiplier is enlarged correspondingly so as to achieve the same effect of increasing the linearity of the side fluorescent light signal.

Please refer to FIG. 11, the side fluorescent light from the fluid chamber 503 passes through the second converging lens 508 to be focused, then the focused side fluorescent light projects on the light sensing area of the third light detector 514. The distance between the third light detector 514 and the forth aperture 512 is adjusted according to the size of the light sensing area of the third light detector 514 to make sure that the facula of the side fluorescent light is small then the light sensing area but occupies the whole light sensing area as large as possible. Shape of the facula of the side fluorescent light is generally circle or ellipse. If the light sensing area is square, facula area of the side fluorescent light should be between 50%-78% of the light sensing area.

On the other hand, when the optical detection device is controlled to detect fluorescent lights, noise issues would be brought out since signal enlargement is conducted. Researches show that noise issue of the silicon photomultiplier is mainly from light crosstalk between dark count and light sensing unit. As disclosed above, the noise issue of dark count could be controlled properly when the light sensing area of the silicon photomultiplier is less than 36 mm$^2$. In some embodiments, light sensing area of the silicon photomultiplier is about 9 mm$^2$, and dark count rate could be controlled under 1 MCPS on the whole. Under above condition, influence of signal pulse could be ignored basically. Therefore, by selecting proper light sensing area, noise issue caused by dark count could be reduced effectively.

Light crosstalk between different light sensing units could be optimized from several approaches disclosed below. For instance, in another embodiment of this application, overvoltage configuration in the optical detection device is optimized for reducing noise issue.

Light crosstalk between different light sensing units happens when photons are released from a light sensing unit at avalanche state and coupled into another light sensing unit as incident photons, which would cause avalanche effect in the latter light sensing unit and generate a current pulse accordingly. At present, crosstalk rate of the silicon photomultiplier generally stays between 5%-10%. In another word, under the condition of ignoring dark count influence, when 100 photons emit into the silicon photomultiplier, current pulses generated accordingly may possibly equal to the ideal current pulse generated from 105-110 incident photons, or rather, noise amplitude generated by light crosstalk between different light sensing units is about 5%-10% of an ideal signal. Above disclosed noise level of the silicon photomultiplier is worse than vacuum photomultiplier.

However, crosstalk rate of the silicon photomultiplier is highly relating to overvoltage applied on the silicon photomultiplier. When crosstalk rate increases, crosstalk rate increases correspondingly. The overvoltage is defined as the difference between reverse bias voltage applied on the silicon photomultiplier and the breakdown voltage of the silicon photomultiplier.

Please refer to FIG. 12, it is found after experiment that crosstalk could be controlled to be less than 1% when the overvoltage is reduced to 1.5V. In this way, the light crosstalk noise of the silicon photomultiplier is superior to the light crosstalk noise of vacuum photomultiplier.

In some embodiments, the reverse bias voltage of the silicon photomultiplier is configured to be slightly larger than the breakdown voltage of the silicon photomultiplier. The overvoltage is defined around 1.5V. However, it should be noted that it is suitable at all to configure the overvoltage below 3V for acquiring a noise level with characteristic matching with the noise level of vacuum photomultiplier. For certain, in some other embodiments, in the condition that the noise level is acceptable, to configure the overvoltage below 5V should be allowable as well.

Meanwhile, in the sample analyzer of this application, noise issue is reduced through temperature control for the silicon photomultiplier. Silicon photomultiplier is a kind of temperature sensitive element, its current gain is varied with temperature obviously. That is because the breakdown voltage of the light sensing diode micro unit is raised with climbing temperature accordingly. If the reverse bias voltage of the silicon photomultiplier stands steady, overvoltage is declined with climbing temperature on the contrary. In the mean time, current gain is positive relating with overvoltage. Therefore, climbing temperature would cause decline of gain. In conclusion, if current gain cannot be maintained constantly, detection result would be influenced in the detection process of the sample analyzer.

In one embodiment, temperature control for the silicon photomultiplier is implemented by applying constant temperature control so as to make the silicon photomultiplier working on a configuration temperature. The configuration temperature is a temperature selected between 20° C. to 40° C., preferably between 20° C. to 40° C. A temperature control device is required for above temperature control solution, including a sealed temperature control chamber, a heater/cooler and a driving controller relating. Of course, additional elements disclosed above would increase the cost and volume of the sample analyzer.

Moreover, it should be understood that reduction of the temperature of the silicon photomultiplier helps to reduce the dark count of the silicon photomultiplier, but quality requirements for the cooler and the temperature control chamber would be stricter correspondingly, which would further raise the cost.

In another embodiment, noise issue is decreased through temperature compensation for the silicon photomultiplier. For example, temperature compensation could be applied for the reverse bias voltage, which means to adjust the reverse bias voltage of the silicon photomultiplier in real time according to current temperature of the silicon photomultiplier so as to remain the reverse temperature constantly. Above temperature compensation solution is implemented only by adjusting the reverse bias voltage of the silicon photomultiplier. It basically increases no cost and volume of the sample analyzer comparing with the temperature control solution. Therefore, in some embodiments, temperature compensation is applied to keep the stability of the current gain of the silicon photomultiplier.

Please refer to FIG. 13, the sample analyzer of the present embodiment includes a temperature compensation device. The temperature compensation device includes a temperature sensor 701, a temperature detection circuit 702, an AD converter 703, a temperature compensation module 704 integrated in the controller 60, a DA converter 705, a voltage adjustment circuit 706 and a regulated power supply 707 with an adjustable output.

The temperature sensor 701 and the temperature detection circuit 702 are used for detecting the environment temperature of the third light detector 514 and generating a temperature signal. The temperature signal is converted as a digital signal by the AD converter 703. The digital signal is transmitted to the controller 60, by which a target value of the reverse bias voltage for the third light detector 514 is calculated by the temperature compensation module 704.

In some embodiments, operation of the temperature compensation module follows below equation:

$$V_{bias}=V_0+k(T-T_0)+V_{OV}$$

Wherein, $V_{bias}$ is defined as the target value of the reverse bias voltage applied on the silicon photomultiplier. $V_0$ is defined as the breakdown voltage of the silicon photomultiplier at temperature k, usually is a constant. T is the current temperature, $V_{OV}$ is the overvoltage. The breakdown voltage of the light sensing diode micro unit 514a is changed from $V_0$ to $V_0+k(T-T_0)$. Therefore, only if the reverse bias voltage on the silicon photomultiplier is adjusted to the target $V_{bias}$, the overvoltage would remain stable correspondingly so as to keep the current gain steady. Both $V_0$ and k could be confirmed on the manual of the silicon photomultiplier. $V_{OV}$ could be configured according to requirements, such as 1.5 V in some embodiments.

After the target value of the reverse bias voltage is confirmed, the controller 60 adjusts the circuit parameters of the voltage adjustment circuit 706 (for instance, it is a feedback voltage in some embodiments.) by controlling the DA converter 705, so as to make the output voltage of the adjustable regulated power supply 707 (rather say, the reverse bias voltage) to reach the target value of the reverse bias voltage.

By using the above sample analyzer to detect blood samples, white blood cell classification could be realized. Moreover, abnormal sample could be detected under above as well, which is shown in FIG. 16. In some embodiment, by using the nucleated red blood cell scatter diagram with nucleated red blood cells count, basophile granulocytes could be detected.

In the sample analyzer of another embodiment of this application, multiple detection modules could be realized. It means, for detecting different kinds of cell particle, different kind of samples are acquired by applying different regents to react with different samples, or different optical detection parameters are applied for samples detection. In particular, because white blood cell and reticulocytes generate fluorescent signals with different strengths respectively after dyed, higher sensitivity would be acquired through applying different optical detection parameters to acquire stable and reliable result. Therefore, above disclosed temperature control device or temperature compensation device are able to keep the current gain of the sample analyzer steady in the detection process under the same detection module. In the mean time, the controller 60 is able to configure different overvoltage according to different detection modules to get different current gains so as to acquire different signal amplifying effects. For example, fluorescent lights generated under reticulocytes detection mode is often weaker than those under the detection module for white blood cell classification. Correspondingly, the controller 60 would adjust overvoltage to increase the current gain under reticulocytes detection module.

However, adjustable range for the current gain of the silicon photomultiplier is generally at five times, but strength differences of fluorescent lights under different detection modules could be over than 10 times. Therefore, for implementing the reticulocytes detection module and the white blood classification on the same sample analyzer, adjustable range for the gain of the silicon photomultiplier is still not satisfied.

For this, in some embodiments, it is acceptable for applying both temperature compensation device and detection circuit to adjust current gain and circuit gain at the same time to satisfy detection requirements under different detection modules.

For instance, in some embodiments, the current/voltage converting amplifier 601c is at least able to configure two circuit gains. Each kind of the circuit gains is corresponding to different measurement modules respectively. When the detection modules of the sample analyzer is changed, the current/voltage converting the amplifier 601c switches between different circuit gains by adjusting current gains through the temperature compensation device.

Of course, in some embodiments, another approach is to keep the current gains steady for controlling the distortion rate, but only change the gain of amplifier to fit the requirements under different detection modules. In addition, in above embodiments, since the circuit gain is far smaller than the current gain, the circuit noise could be ignored so as to control signal/noise rate.

In some embodiments, it is also workable to change the power of the light source 501 under different detection modules to implement the calibration for the scatter diagram position. For example, the power of the light source 501 under white cell classification detection module is selected optimally as 5 mW, and the laser power under the reticulocytes detection mode is configured as 15 mW. However, the power increase of the light source 501 causes cost climbing correspondingly.

In one embodiment for detecting a sample containing reticulocytes using the sample analyzer of this application, under the configuration of a reticulocytes detection mode of the sample analyzer, a scatter diagram of reticulocytes is acquired according to side fluorescent strength information and forward diffusion light strength information. Mature red blood cells, reticulocytes, platelets and white blood cells could be distinguished from the scatter diagram of reticulocytes under above disclosed.

In the same way, for another embodiment, it is also workable to detect a sample containing nucleated red cells and white blood cells under nucleated red cell mode. Nucleated red cells, white blood cells and basophile granulocytes are distinguished according to the scatter diagram of nucleated red cells based on side fluorescent light strength information and forward diffusion light strength information. The result is shown in FIG. 18.

Detection result could be displayed on the screenshot of the sample analyzer or transmitted to a computer for displaying as well. It is decided based on the detection requirements and the configuration of the sample analyzer.

In another embodiment of this application, a sample analysis method for a sample analyzer is disclosed, which includes:

providing a sample, the sample includes cell particles processed by a reagent;

providing an optical measurement device, the optical measurement device includes a fluid chamber, a light source and a light detector including at least one silicon photomultiplier;

when the sample forms a sample stream and flows through the fluid chamber, the light source illuminates the sample stream flowing through the fluid chamber to generate a light signal and the light detector receives the light signal and transforms the light signal into an electrical signal; and classifying the cell particles according to the electrical signal.

Detection for the sample containing white blood cell, reticulocytes and nucleated red blood cell is selected for instance and described below. As above disclosed method, a processed sample is provided to the optical detection device. The sample stream flows through the fluid chamber and is illuminated by the light source with 5-15 mW power to generate light signal. The silicon photomultiplier in the light detector has several arrays including multiple light sensing units respectively. The light sensing area of each light sensing unit is small than the imaging area of a single cell particle. A reverse bias voltage larger than the breakdown voltage is applied on the light sensing unit. The light detector receives the light signal and transforms the light signal into an electrical signal. Each electrical signal reflects the strength of the optical signal of each cell particle, such as the strength of the fluorescent light. Differences of those electrical signals are utilized to classify and count the cell particles.

In another embodiment, the reverse bias voltage of the optical detection device could be configured according to different operation modes. For example, a first reverse bias voltage is applied on the light sensing unit when the cell particles waiting for detecting are white blood cells, and a second reverse bias voltage is applied on the light sensing unit when the cell particles waiting for detecting are reticulocytes. The first reverse bias voltage is small than the second reverse bias voltage so that a better sensitivity is ensured for the detection of the reticulocytes. In addition, different amplifier gains could be configured according to different modes.

After clinical performance evaluation, the sample analyzer disclosed in the embodiments of this application conducts tests for white blood cell classification count, reticulocytes count, nucleated blood cell count and warming ability for abnormal sample. The result of above tests is consistent well with the same tests conducted by the blood cell analyzer.

Above descriptions is disclosed under the examples of fluorescent lights detection. However, the above disclosed optical measurement device is also workable for detecting other types of faint lights, such as side diffusion lights or light absorption signal.

In some other embodiments, the sample analyzer is able to include multiple light sources so that multiple paths of fluorescent lights or faint lights are formed. The silicon photomultiplier could be applied as a light detector to detect above fluorescent lights or faint lights and combine above fluorescent lights or faint lights with diffusion lights to implement detections for different cell particles and feature information on particles surface.

In some other embodiments, the sample analyzer is also able to be applied for other kinds of sample, but not limits for blood sample detection only.

In some other embodiments, multiple silicon photomultipliers could be integrated to form a silicon photomultiplier array with sufficient area and number of light sensing units to satisfy user requirements.

It is understandable for the skilled in the art that all or some of the processes disclosed in the embodiments of the present application are able to be implemented by instructing relating hardware through computer programs. Above programs are able to be stored in a readable storing media of computer. Above programs are able to include the implement of all flow charts for all methods disclosed in above embodiments in execution. The readable storing media include but not limited to select from below: Hard Disc, Optical Disc, Read-Only Memory (ROM) and Random Access Memory (RAM).

Although the present disclosure has been described through specific embodiments, the present disclosure is not limited to the specific embodiments described above. Those of skill in the art should understand that various modifications, alternatives and variations may be made based on the present disclosure, which all should be within the scope of protection of the present disclosure. Furthermore, "a (an) embodiment" or "another embodiment" mentioned above may represent different embodiments, or may also be combined completely or partly in one embodiment.

The invention claimed is:

1. A sample analyzer, comprising:
 a sample collection device for collecting a sample quantitatively, wherein the sample comprises cell particles;
 a reagent supplement device for providing a reagent, wherein the reagent is able to react with the cell particles;
 a sample reaction device for receiving the sample from the sample collection device and the reagent from the reagent supplement device, wherein the reagent reacts with the cell particles to generate an analyte;
 an analyte delivery device for delivering the analyte for optical measurement; and
 an optical measurement device for measuring a light signal generated from the analyte to generate light signal information, wherein the optical measurement device comprises:
 a fluid chamber comprising an illumination zone, wherein the analyte from the analyte delivery device flows through the illumination zone to form a sample stream;
 a light source for illuminating the illumination zone to generate the light signal from the sample stream; and
 a light detector for detecting the light signal and transforming the light signal into the light signal information, wherein the light detector comprises at least one silicon photomultiplier, wherein a light sensing area of the silicon photomultiplier is smaller than a threshold value, a distortion of a pulse amplitude of an electrical signal is triggered when the light sensing area of the silicon photomultiplier exceeds the threshold value, and the electrical signal is generated according to an amount of a dark pulse count overlapping on a single one of the cell particles.

2. The sample analyzer of claim 1, wherein the light source comprises a laser generator, the output power of the laser generator is between 1 to 20 mW.

3. The sample analyzer of claim 1, wherein the light source comprises a laser generator, the output power of the laser generator is between 1 to 15 mW.

4. The sample analyzer of claim 1, wherein the silicon photomultiplier comprises a plurality of light sensing units arranged in an array configuration, an illumination area of each light sensing unit is smaller than an imaging area of a single cell particle, a size of the light sensing unit is between 10 μm to 50 μm.

5. The sample analyzer of claim 1, wherein the silicon photomultiplier comprises a plurality of light sensing units arranged as array configuration, the number of the light sensing units is larger or equal to 500 units.

6. The sample analyzer of claim 1, wherein the silicon photomultiplier comprises a plurality of light sensing units arranged as array configuration, preferably, the number of the light sensing units is larger or equal to 1280 units.

7. The sample analyzer of claim 1, wherein a light sensing area of the silicon photomultiplier is between 1-36 mm2, the light sensing area is a circle with a diameter between 2 mm to 6 mm.

8. The sample analyzer of claim 1, wherein a light sensing area of the silicon photomultiplier is between 1-36 mm2, the light sensing area is a square with a length between 1 mm to 6 mm.

9. The sample analyzer of claim 1, wherein the optical measurement device further comprises: an optical path, configured between the fluid chamber and the light detector, for converging the light signal to form a facula on a light sensing area of the silicon photomultiplier, the facula is between 50% to 78% of the light sensing area.

10. The sample analyzer of claim 1, further comprising a controller for controlling a reverse bias voltage applied on the silicon photomultiplier to keep an overvoltage between 0 to 5 volt, the overvoltage is a differences between the reverse bias voltage and a breakdown voltage of the silicon photomultiplier.

11. The sample analyzer of claim 10, wherein the controller adjusts the reverse bias voltage applied on the silicon photomultiplier according to different operation modes to control the overvoltage.

12. The sample analyzer of claim 1, further comprising a temperature control device for controlling a temperature of the silicon photomultiplier at a configuration temperature, the configuration temperature is selected between 20° C. to 40° C.

13. The sample analyzer of claim 1, further comprising a temperature compensation device for adjusting a reverse bias voltage applied on the silicon photomultiplier according to a temperature of the silicon photomultiplier so as to keep an overvoltage constant.

14. The sample analyzer of claim 13, wherein the temperature compensation device comprises a temperature sensor, a temperature detection circuit, an AD converter, a temperature compensation module, a DA converter, a voltage adjustment circuit and a regulation power supply with an adjustable output, wherein the temperature sensor and the temperature detection circuit detect the temperature of the silicon photomultiplier and generate a temperature signal, the AD converter converters the temperature signal into a digital signal, the temperature compensation module calculates a target value of the reverse bias voltage of the silicon photomultiplier, the controller adjusts a circuit parameter of the voltage adjustment circuit by controlling the DA converter to cause an output voltage of the adjustable regulation power supply to reach the target value of the reverse bias voltage.

15. A sample analyzer, comprising:
   a sample collection device for collecting a sample quantitatively, wherein the sample comprises cell particles;
   a reagent supplement device for providing a reagent, wherein the reagent is able to react with the cell particles;
   a sample reaction device for receiving the sample from the sample collection device and the reagent from the reagent supplement device, wherein the reagent reacts with the cell particles to generate an analyte;
   an analyte delivery device for delivering the analyte for optical measurement; and
   an optical measurement device for measuring a light signal generated from the analyte to generate light signal information, wherein the optical measurement device comprises:
   a fluid chamber comprising an illumination zone, wherein the analyte from the analyte delivery device flows through the illumination zone to form a sample stream;
   a light source for illuminating the illumination zone to generate the light signal from the sample stream;
   a light detector for detecting the light signal and transforming the light signal into the light signal information, wherein the light detector comprises at least one silicon photomultiplier; and
   a controller for controlling a reverse bias voltage applied on the silicon photomultiplier to keep an overvoltage between 0 to 5 volts, the overvoltage is a differences between the reverse bias voltage and a breakdown voltage of the silicon photomultiplier.

16. A sample analyzer, comprising:
   a sample collection device for collecting a sample quantitatively, wherein the sample comprises cell particles;
   a reagent supplement device for providing a reagent, wherein the reagent is able to react with the cell particles;
   a sample reaction device for receiving the sample from the sample collection device and the reagent from the reagent supplement device, wherein the reagent reacts with the cell particles to generate an analyte;
   an analyte delivery device for delivering the analyte for optical measurement; and
   an optical measurement device for measuring a light signal generated from the analyte to generate light signal information, wherein the optical measurement device comprises:
   a fluid chamber comprising an illumination zone, wherein the analyte from the analyte delivery device flows through the illumination zone to form a sample stream;
   a light source for illuminating the illumination zone to generate the light signal from the sample stream;
   a light detector for detecting the light signal and transforming the light signal into the light signal information, wherein the light detector comprises at least one silicon photomultiplier; and
   a temperature compensation device for adjusting a reverse bias voltage applied on the silicon photomultiplier according to a temperature of the silicon photomultiplier so as to keep an overvoltage constant.

* * * * *